United States Patent [19]

Goudie et al.

[11] 4,382,094

[45] May 3, 1983

[54] REDUCED NAPHTHALENES, THEIR PREPARATION AND USE

[75] Inventors: Alexander C. Goudie, Harlow; Josephine M. Cox, Stevenage, both of England

[73] Assignee: Beecham Group Limited, England

[21] Appl. No.: 288,178

[22] Filed: Jul. 29, 1981

[30] Foreign Application Priority Data

Jul. 30, 1980 [GB] United Kingdom ............... 8024971

[51] Int. Cl.$^3$ ..................................... A61K 31/135
[52] U.S. Cl. ........................... 424/330; 260/465 F; 260/465 R; 549/78; 549/445; 549/497; 560/256; 562/462; 564/217; 564/428; 424/275; 424/278; 424/282; 424/305; 424/317; 424/320; 424/331; 568/327
[58] Field of Search ............... 564/428; 568/327; 260/340.5 R; 424/331, 330

[56] References Cited

U.S. PATENT DOCUMENTS

| | | | |
|---|---|---|---|
| 3,833,726 | 9/1974 | Schwender et al. | 568/327 |
| 3,843,665 | 10/1974 | Coombs et al. | 568/327 |
| 4,177,271 | 12/1979 | Vallet | 542/429 |
| 4,201,869 | 5/1980 | Cohen et al. | 568/327 |

*Primary Examiner*—Ethel G. Love

*Attorney, Agent, or Firm*—Jacobs & Jacobs

[57] ABSTRACT

A compound of the formula (I) and pharmaceutically acceptable salts thereof:

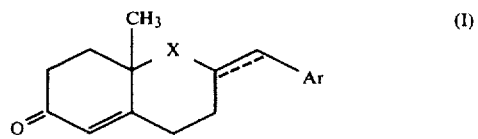

wherein:

Ar is phenyl, optionally substituted by one or more $C_{1-4}$ alkyl, $C_{1-4}$ alkoxy, halogen, cyano, nitro, hydroxy, $CONH_2$, $CO_2W$ wherein W is $C_{1-6}$ alkyl or $C_{1-4}$ alkylphenyl which phenyl may be substituted by one or more $C_{1-4}$ alkyl, $C_{1-4}$ alkoxy or halogen, $NR_1R_2$ wherein $R_1$ and $R_2$ are selected from hydrogen or $C_{1-6}$ alkyl, NHCO $C_{1-6}$ alkyl or $C_{1-6}$ alkylcarbonyloxy; phenyl disubstituted on adjacent carbon atoms by methylenedioxy; furyl or thienyl;

the dotted lines represent an optionally present double bond; and

X is CO or $CR_1OH$ wherein $R_1$ is hydrogen or $C_{1-4}$ alkyl, having useful pharmacological activity, processes for their preparation and their use.

9 Claims, No Drawings

REDUCED NAPHTHALENES, THEIR PREPARATION AND USE

This invention relates to reduced naphthalenes, their preparation and use.

Topical anti-inflammatories are of use in the treatment of a large number of inflammatory skin conditions and inflammatory conditions of the eyes, ears, nose and throat. Most topical anti-inflammatories used to date are steroids. These compounds have proven to be very effective but they tend to have a number of side effects. Many physicians consider these side effects so serious as to severely limit the applicability of the steroids. Clearly it would be desirable to find topical anti-inflammatory agents that were free of steroidal side effects.

The present invention provides a compound of the formula (I) and pharmaceutically acceptable salts thereof:

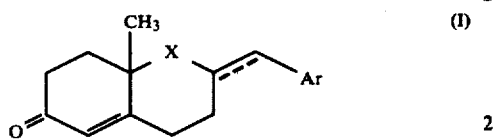

wherein:

Ar is phenyl, optionally substituted by one or more $C_{1-4}$ alkyl, $C_{1-4}$ alkoxy, halogen, cyano, nitro, hydroxy, $CONH_2$, $CO_2W$ wherein W is $C_{1-6}$ alkyl or $C_{1-4}$ alkylphenyl which phenyl may be substituted by one or more $C_{1-4}$ alkyl, $C_{1-4}$ alkoxy or halogen, $NR_1R_2$ wherein $R_1$ and $R_2$ are selected from hydrogen or $C_{1-6}$ alkyl, NHCO $C_{1-6}$ alkyl or $C_{1-6}$ alkylcarbonyloxy; phenyl disubstituted on adjacent carbon atoms by methylenedioxy; furyl or thienyl;

the dotted lines represent an optionally present double bond; and

X is CO or $CR_1OH$ wherein $R_1$ is hydrogen or $C_{1-4}$ alkyl.

Suitable examples of Ar when optionally substituted phenyl include phenyl, and phenyl substituted by methyl, ethyl, methoxy, ethoxy, chlorine, bromine, cyano, nitro, hydroxy, carboxy, $CONH_2$ or $NR^1_1R^1_2$ wherein $R_1^1$, $R_2^2$ are selected from hydrogen and methyl; and phenyl disubstituted on adjacent carbon atoms by methylenedioxy.

Favourably Ar is unsubstituted phenyl, or phenyl monosubstituted by methoxy, chloro, nitro, hydroxy, $NMe_2$ or 3,4 disubstituted by hydroxy or methylenedioxy.

Ar when substituted is often 3 or 4 substituted.

Often, Ar when thiophene or furan is attached at the 2-position.

Preferably the exocyclic optional double bond will be present.

Within X, suitable examples of the variable group $R_1$ include hydrogen and methyl and ethyl. X is favourably CO, CHOH or $C(CH_3)OH$.

The compounds of the formula (I) may form conventional salts. The nature of these salts of course depends on whether the particular compound of the formula (I) contains acidic or basic groups.

In the former case the compound can form salts with alkali and alkaline earth metals, suitably sodium and potassium, and ammonium and substituted ammonium salts.

In the latter case the compound can form acid addition salts with acids, such as preferably the conventional pharmaceutically acceptable acids, for example hydrochloric, hydrobromic, phosphoric, acetic, fumaric, salicylic, citric, lactic, mandelic, tartaric and methanesulphonic acids.

It will of course be realised that the compounds of the formula (I) have asymmetric centres, and thus care capable of existing in a number of stereoisomeric forms. For example, compounds of the formula (I) wherein the exocyclic double bond is not present has an asymmetic centre at the 6-position. The invention extends to each of these stereoisomeric forms, and to mixtures thereof. The different stereoisomeric forms may be separated one from the other by the usual methods, such as by chromatography.

There is a group of compounds within formula (I) wherein Ar is phenyl, optionally substituted by $C_{1-4}$ alkyl, $C_{1-4}$ alkoxy or halogen; furyl or thienyl;

the dotted line in formula (I) represents an optionally present double bond; and X is CO or $CR_1OH$ wherein $R_1$ is hydrogen or $C_{1-4}$ alkyl;

From the aforesaid it will be appreciated that there is a sub-group of formula (II) within formula (I):

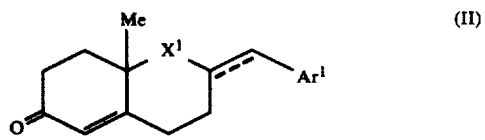

wherein the variables are as defined in formula (I), except for $Ar^1$ which is phenyl or substituted phenyl and $X^1$ which is $CR_1OH$ as defined in formula (I).

Suitable and favourable examples of the variables in formula (II) include those described in relation to formula (I).

More suitable compounds of the formula (II) are those wherein $Ar^1$ is optionally substituted phenyl and the exocyclic double bond is present.

$X^1$ is preferably CHOH or $C(CH_3)OH$.

A second sub-group of compounds within formula (I) is of formula (III):

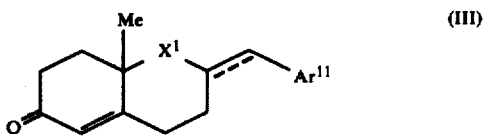

wherein the variables are as defined in formula (I) and (II) except for $Ar^{11}$ furyl or thienyl.

Suitable examples of the variables in formula (III) are as described in relation to formula (I).

Yet another useful sub-group of compounds within the formula (I) is of formula (IV):

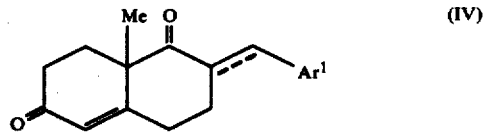

wherein the variables are as defined in formula (II).

Suitable and favourable examples of the variables in formula (IV) are as described in relation to formula (I) and (II).

One suitable group of compounds within formula (IV) is of formula (V):

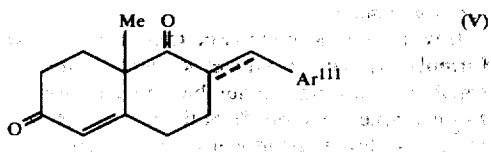

wherein the variables are as defined in formula (IV) except for $Ar^{III}$ which is phenyl or phenyl substitute by methyl, ethyl, methoxy, chlorine, bromine, cyano or nitro.

Suitable, favourable and preferred values for the variables are as described under formula (IV).

$Ar^{III}$ when substituted phenyl is usually 3 or 4 substituted, preferably 3-substituted.

A more suitable group of compounds within formula (IV) is of formula (VI):

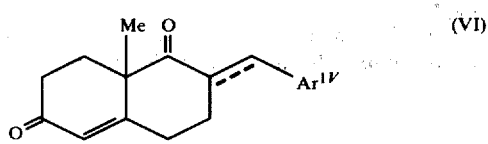

wherein the variables are as defined in formula (IV) except for $Ar^{IV}$ which is phenyl substituted by hydroxy, carboxy, $CONH_2$ or $NR^1{}_1R_2{}^1$ wherein $R^1{}_1$ and $R^1{}_2$ are selected from hydrogen and methyl; and phenyl disubstituted on adjacent carbon atoms by methylenedioxy.

Suitable, favourable and preferred values for the variables are as described under formula (IV).

A further sub-group of interest within formula (I) is of formula (VII):

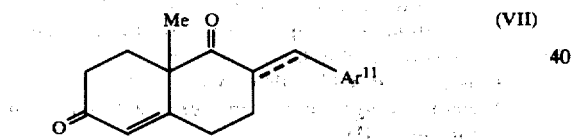

wherein the variables are as defined in formula (III).

Suitable examples of the variables in formula (V) are as described in relation to formulae (III) and (IV).

The present invention provides a pharmaceutical composition adapted for topical administration which comprises a compound of the formula (I) and a pharmaceutically acceptable carrier therefor.

The compounds of the invention will normally be made up into a cream, lotion, gel or ointment for topical administration to the skin comprising a compound of the formula (I) which has been formulated as a cream, lotion, gel or ointment.

Cream, lotion, gel or ointment formulations that may be used for compounds of the formula (I) are conventional formulations well known in the art, for example, as described in standard text books of pharmaceutics and cosmetics, such as Harry's Cosmeticology published by Leonard Hill Books, and the British Pharmacopoeia. A standard emulsifying ointment base or an anhydrous polyethylene glycol are simple examples of such suitable formulations.

The compositions of this invention may be used in the topical treatment of atopic and contact dermatitis, psoriasis, eczema and other inflammatory dermatoses and in inflammatory conditions of eyes, ears, nose and throat.

It will be appreciated that the amount of the compound of the formula (I) used will depend on a number of factors such as the nature and severity of the disorder being treated, and the specific compound being used. However, by way of illustration it is believed that effective therapy can be achieved using roughly similar amounts of the compounds of formula (I) as would be used of hydrocortisone. A typical formulation will suitably contain 0.1 to 10%, more suitably 0.5 to 5% of the compound of formula (I).

The compositions of this invention may also contain other therapeutic agents such as anti-infective agents. Suitable anti-infective agents include the topically applicable antibacterial, anti-yeast and anti-fungal agents already in use in topical anti-inflammatory preparation.

The invention further provides a method of treatment or prophylaxis of inflammation in mammals including man which comprises the topical administration of a therapeutically effective amount of a compound of formula (I) or a pharmaceutically acceptable salt thereof.

The present invention also provides a process for the preparation of a compound of formula (I), which process comprises the base catalysed reaction of a compound of formula (VIII):

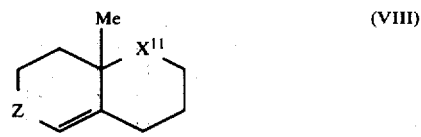

wherein $X^{11}$ is CO and Z is CO or protected CO with a compound of formula (IX):

wherein (i) P and Q together form an oxo group; to give a compound of formula (I) or (X) as hereinafter defined wherein X is CO and the exocyclic double bond is present; or (ii) P is hydrogen and Q is halogen, such as bromine to give a compound of formula (I) or (X) wherein X is CO and the exocyclic double bond is not present; and thereafter if desired or necessary converting the $X^{11}$ carbonyl group to $CR_1OH$ and/or reducing an exocyclic double bond when present and/or converting a compound of formula (I) to another compound of formula (I) and/or deprotecting a protected carbonyl group and/or forming a pharmceutically acceptable salt.

The coupling reaction between compounds of formula (VIII) and (IX) wherein P and Q form an oxo group may be carried out in a suitable solvent such as water, methanol or ethanol using a base such as potassium hydroxide as catalyst.

The coupling reaction between compounds of formula (VIII) and (IX) wherein P is hydrogen and Q is halogen may be carried out in an inert solvent such as tetrahydrofuran or ether using a strong base such as lithium diisopropylamide. In this case a mixture of isomers of the compound of formula (I) or (X) is obtained which may be separated by chromatographic methods.

The subsequent variation of the X group an the exocyclic double bond may be carried out as follows:

(a) A compound wherein X is CO may be reduced (with for example lithium aluminium hydride, or reacted with an alkyl Grignard, alkyl lithium or other metal derivative, to give the corresponding X is $CR_1OH$ compound.

(b) A compound in which the exocyclic double bond is present may be reduced to the corresponding compound wherein this double bond is not present. Suitable reducing agents are lithium aluminium hydride/cuprous iodide complex (E. C. Ashby and J. J. Lin, Tetrahydron Letters 1975, 50, 4453) or other complexes of copper (I) hydride such as n-pentyne (R. K. Boeckman and R. Michalak, J. Amer. Chem. Soc., 1974, 96, 1623.

It will be readily apparent that if desired some compounds of formula (I) prepared in this way may subsequently be converted into other compounds of the formula (I). For example, compounds of the formula (I) wherein Ar is disubstituted by methylendioxy may be converted to compounds where Ar is disubstituted on adjacent carbon atoms by hydroxy by cleavage with a Lewis acid such as boron tribromide in a solvent such as dichloromethane.

The de-protection reaction may be carried out in conventional manner, for example as described in "Steroid Reactions" by C. Djerassi, Chapter 1, p. 1–87.

The group Z when protected CO will favourably be a dithioketal such as ethylene dithioketal. In this case it is convenient to use thallium trinitrate in methanol to effect removal of the thioketal group.

Compounds of formulae (VIII) and (IX) are either known compounds or may be made in analogous manner to known compounds.

It will be appreciated from the foregoing that the present invention further provides a process for the preparation of a compound of formula (I) which process comprises the deprotection of a compound of formula (X):

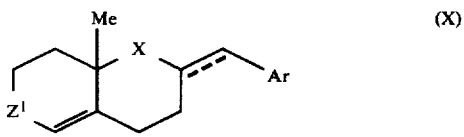

wherein $Z^1$ is protected CO and the remaining variables are as defined in formula (I).

The deprotection reaction may be carried out as hereinbefore described.

Favourable values for $Z^1$ are as hereinbefore described for Z when protected CO.

Compounds of formula (X) are novel compounds, are useful intermediates, and as such form an important part of this invention.

The following Descriptions illustrate the preparation of intermediates.

The following Examples illustrate the preparation of compounds of the formula (I).

DESCRIPTION 1

6'-Benzylidene-3',4',4'a,6',7',8'-hexahydro-4'a-methyl-spiro[1,3-diothiolane-2,2'(5'H)-naphthalen]-5'-one

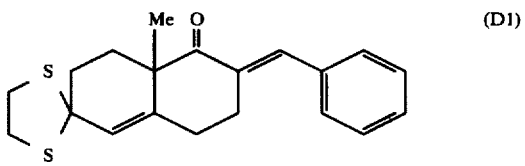

A solution of 3',4',4'a,6'7',8'-hexahydro-4'a-methyl-spiro[1,3-diothiolane-2,2'(5H)-naphthalen]-5'-one[1](5.0 g, 0.02 mole), benzaldehyde (2.5 g, 0.024 mole) and potassium hydroxide (2.5 g) in water was refluxed for 2 days. On cooling, a white solid precipitated which was filtered and recrystallised from ether to give the title compound as a white, crystalline solid, (4.8 g, 72%) m.p. 116°–118° C.

I.R. 1680 cm$^{-1}$

N.M.R. (CDCl$_3$)δ: 1.27 (3H, s), 1.84–2.74 (8H, m), 3.27 (4H, s), 5.67 (1H, s), 7.3 (5H, bs), 7.44 (1H, bs).

Reference 1: R. A. J. Smither and D. J. Hannah, Synth. Commun., 1979, 9(4), 301–311.

DESCRIPTION 2

6'-(2-Thienylmethylidene)-3',4',4'a,6',7',8'-hexahydro-4'a-methyl-spiro[1,3-dithiolane-2,2'(5'H)-naphthalen]-5'-one

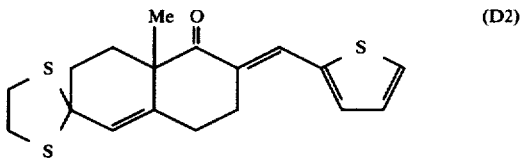

A solution of 3',4',4'a,6',7',8'-hexahydro-4'a-methyl-spiro[1,3-dithiolane-2,2'(5'H)-haphthalen]-3'-one[1](2.0 g, 0.0079 mole), thiophene-2-carboxaldehyde (1.32 g, 0.012 mole) and potassium hydroxide (0.7 g) in water containing a small quantity of methanol was refluxed for 2 hours. This gave the title compound as a pale yellow solid which precipitated on cooling. This was filtered off and dried in vacuo (2.1 g, 78%), m.p. 131°–133° C.

N.M.R. (CDCl$_3$)δ: 1.3 (3H, s), 1.7–2.8 (8H, m), 3.3 (4H, m), 5.67 (1H, s), 6.9–7.5 (3H, m), 7.7 (1H, bs).

Reference 1: R. A. J. Smither and D. J. Hannah, Synth Commun, 1979, 9(4), 301–311.

DESCRIPTION 3

6'-Benzylidene-3',4',4'a,6',7',8'-hexahydro-5'a-hydroxy-4'-methyl-spiro[1,3-dithiolane-2,2'-naphthalene]

(Intermediate for Example 14)

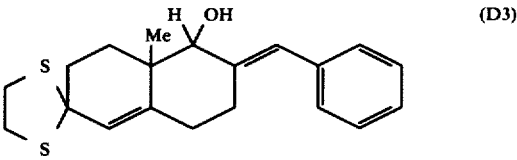

6'-Benzylidene-3',4',4'a,6',7',8'-hexahydro-4'a-methyl-spiro[1,3-dithiolane-2,2'(5'H)-naphthalen]5'-one (D1) (1.0 g, 0.003 mole) was added to a suspension of lithium aluminum hydride (0.11 g, 0.003 mole) in dry ether (25 ml) under nitrogen. The mixture was stirred for 2 hours at room temperature. Excess lithium aluminium hydride was destroyed by the addition of water (1 ml) and 10% sodium aqueous hydroxide (3 ml). The lithium salts were filtered off and washed with ether (10 ml). The organic phase was dried ($Na_2SO_4$) and the solvent was removed to give the title compound (1.0 g, 100%) as a white crystalline solid.

N.M.R. ($CDCl_3$)δ: 1.0 (3H, s), 1.53–2.36 (8H, m), 3.3 (4H, s), 3.9 (1H, s), 5.58 (1H, s), 6.53 (1H, s), 7.2 (5H, s), 7.23 (1H, s).

DESCRIPTION 4

6'-Benzylidene-3',4',4'a,6',7',8'-hexahydro-5'a-hydroxy-4'a,5'a-dimethyl-spiro[1,3-dithiolane-2,2'-naphthalene]- (Intermediate for Example 15)

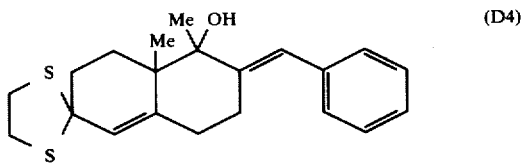

(D4)

Methyl lithium (0.096 g, 2.7 ml of a 1.6 M solution in ether, 0.0044 mole) was added dropwise to a solution of 6'-benzylidene-3',4',4'a,6',7',8'-hexahydro-4'a-methyl-spiro[1,3-dithiolane-2,2'(5'H)-naphthalen]5'-one (D1) (1.5 g, 0.0044 mole) in dry tetrahydrofuran (25 ml) at −78° C. under nitrogen. This was allowed to reach room temperature, poured into water (50 ml) acidified with 1N hydrochloric acid (15 ml) and extracted with chloroform (100 ml). After drying ($Na_2SO_4$), the solvent was evaporated to give the title compound as a white crystalline solid (1.35 g, 86%).

N.M.R. ($CDCl_3$)δ: 1.1 (3H, s), 1.3 (3H, s), 1.8–2.4 (8H, m), 3.3 (4H, s), 5.56 (1H, s), 6.56 (1H, s), 7.13 (5H, s).

EXAMPLE 1

2-Benzylidene-3,4,8,8a-tetrahydro-8a-methyl-1,6(2H,7H)-naphthalenedione

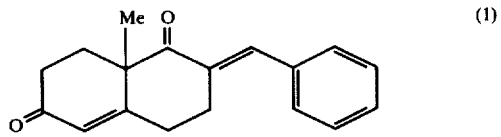

(1)

Thallium (III) nitrate trihydrate (0.88 g, 2 mmole) in methanol (20 ml) was added in one portion to the thioacetal of Description 1 (D1) (0.684 g, 2 mmole) in tetrahydrofuran (4 ml). A pale yellow precipitate formed immediately and was filtered off after 5 minutes. The filtrate was poured into water and extracted with ether, dried ($Na_2SO_4$) and evaporated to give a yellow gum. This was purified by column chromatography on silica gel using ether as eluant, which gave the title compound as an off-white solid (0.24 g, 43%) m.p. 88° C.

N.M.R. ($CDCl_3$)δ: 1.49 (3H, s), 2.02–3.06 (8H, m), 5.9 (1H, s), 7.4 (5H, s), 7.65 (1H, bs).

Found M+, 266.1317. Calc. for $C_{18}H_{18}O_2$: 266.1307.

EXAMPLE 2

2-(2-Thienylmethylidene)-3,4,8,8a-tetrahydro-8a-methyl-1,6(2H,7H)-naphthalenedione

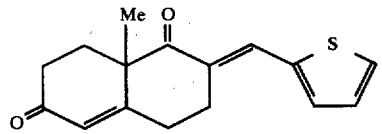

(2)

Thallium (III) nitrate trihydrate (1.28 g, 0.0029 mole) in methanol (30 ml) was added in one portion to the thioacetal of Description 2 (D2) (1.0 g, 0.0029 mole) in tetrahydrofuran (6 ml). A pale yellow precipitate formed immediately and was filtered off after 5 minutes. The filtrate was diluted with water, extracted with diethyl ether, dried ($Na_2SO_4$) and evaporated to produce a yellow gum. This was chromatographed on silica gel using diethyl ether/n-pentane:7/3 as eluant, which gave the title compound as a pale yellow solid (0.34 g, 44%) m.p. 107° C.

N.M.R. ($CDCl_3$)δ: 1.5 (3H, s), 2.0–2.9 (8H, m), 5.85 (1H, s), 7.0–7.6 (3H, m), 7.8 (1H, bs).

The compounds of Example No's 3–15 in Table 1 were prepared in an analogous manner to Examples 1 and 2 using the appropriate thioacetal, prepared in an analogous manner to Descriptions 1 and 2.

TABLE 1

| Compound No. | X | Ar |
|---|---|---|
| 1 | CO | $C_6H_5$ |
| 2 | CO | 2-thienyl |
| 3 | CO | 4-Cl $C_6H_4$ |
| 4 | CO | 2-furyl |
| 5 | CO | 3-Cl $C_6H_4$ |
| 6 | CO | 4-CN $C_6H_4$ |
| 7 | CO | 4-$NO_2C_6H_4$ |
| 8 | CO | 4-$NMe_2C_6H_4$ |
| 9 | CO | 3,4-methylenedioxy $C_6H_3$ |
| 10 | CO | 3-OH $C_6H_4$ |
| 11 | CO | 4-OMe $C_6H_4$ |
| 12 | CO | 4-Me $C_6H_4$ |
| 13 | CO | 4-COOH $C_6H_4$ |
| 14 | CHOH | $C_6H_5$ |
| 15 | C($CH_3$)OH | $C_6H_5$ |

EXAMPLE 3

2-(4-Chlorobenzylidene)-3,4,8,8a-tetrahydro-8a-methyl-1,6-(2H,7H)-naphthalenedione m.p. 121°–123° C.

N.M.R. ($CDCl_3$)δ: 1.47 (3H, s), 2.0–3.2 (8H, m), 5.82 (1H, s), 7.28 (4H, s), 7.48 (1H, s).

Found M+, 300.0913. Calc. for $C_{18}H_{17}ClO_2$, 300.0917.

EXAMPLE 4

2-(2-Furylmethylidene)-3,4,8,8a-tetrahydro-8a-methyl-1,6(2H,7H)-naphthalenedione m.p. 109°–110° C.

N.M.R. ($CDCl_3$) δ: 1.45 (3H, s), 1.9–3.2 (8H, m), 5.80 (1H, s), 6.40–6.67 (2H, m), 7.28 (1H, s), 7.52 (1H, s).

Found M+, 256.1101. Calc. for $C_{16}H_{16}O_3$, 256.1099.

EXAMPLE 5

2-(3-Chlorobenzylidene)-3,4,8,8a-tetrahydro-8a-methyl-1,6-(2H,7H)-naphthalenedione m.p. 111°–2° C.

N.M.R. (CDCl$_3$) δ: 1.47 (3H, s), 2.0–3.2 (8H, m), 5.83 (1H, s), 7.25 (4H, bs), 7.47 (1H, s).

Found: C, 71.52; H, 5.61; Cl, 11.72%. Requires: C, 71.88; H, 5.66; Cl, 11.81%.

EXAMPLE 6

4-[(3,4,8,8a-Tetrahydro-8a-methyl-1,6-dioxo(2H,7H)-naphthalen-2-yl)methylidene]benzonitrile m.p. 143°–5° C.

N.M.R. (CDCl$_3$) δ: 1.48 (3H, s), 1.9–3.3 (8H, m), 5.83 (1H, s), 7.27–7.77 (5H, m).

Found M$^+$, 291.1241. Calc. for C$_{19}$H$_{17}$NO$_2$, 291.1259.

EXAMPLE 7

4-[(3,4,8,8a-Tetrahydro-8a-methyl-1,6-dioxo(2H,7H)-naphthalen-2-yl)methylidene]nitrobenzene m.p. 156°–7° C.

N.M.R. (CDCl$_3$) δ: 1.5 (3H, s), 2.0–3.2 (8H, m), 5.83 (1H, s), 7.81 (4H, q), 7.54 (1H, s).

Found M$^+$, 311.1551. Calc. for C$_{18}$H$_{17}$NO$_4$, 311.1158.

EXAMPLE 8

2-(4-Dimethylaminobenzylidene)-3,4,8,8a-tetrahydro-8a-methyl-1,6(2H,7H)-naphthalenedione m.p. 163°–5° C.

N.M.R. (CDCl$_3$) δ: 1.47 (3H, s), 2.0–2.78 (8H, m), 2.95 (6H, s), 5.86 (1H, s), 6.93 (4H, q), 7.5 (1H, s).

Found M$^+$, 309.1752. Calc. for C$_{20}$H$_{23}$NO$_2$, 309.1729.

EXAMPLE 9

2-(3,4-Methylenedioxybenzylidene)-3,4,8,8,a-tetrahydro-8a-methyl-1,6(2H,7H)-naphthalenedione m.p. 98°–9° C.

N.M.R. (CDCl$_3$) δ: 1.44 (3H, s), 2.0–3.3 (8H, m), 5.8 (1H, s), 5.87 (2H, s), 6.78 (1H, s), 6.8 (2H, s), 7.42 (1H, bs).

Found M$^+$, 310.1218. Calc. for C$_{19}$H$_{18}$O$_4$, 310.1205.

EXAMPLE 10

2-(3-Hydroxybenzylidene)3,4,8,8a-tetrahydro-8a-methyl-1,6(2H,7H)-naphthalenedione m.p. 186°–7° C.

N.M.R. (CD$_3$OD) δ: 1.5 (3H, s), 1.95–3.10 (8H, m), 5.9 (1H, s), 6.7–7.4 (4H, m), 7.52 (1H, s).

EXAMPLE 11

2-(4-Methoxybenzylidene)-3,4,8,8a-tetrahydro-8a-methyl-1,6(2H,7H)-naphthalenedione m.p. 111°–113° C.

N.M.R. (CDCl$_3$) δ: 1.45 (3H, s), 2.0–3.2 (8H, m), 3.75 (3H, s), 5.8 (1H, s), 7.06 (4H, q), 7.52 (1H, s).

Found: C, 77.00; H, 7.04%. Requires: C, 77.03; H, 6.76%.

EXAMPLE 12

2-(4-Methylenzylidene)-3,4,8,8a-tetrahydro-8a-methyl-1,6(2H,7H)-naphthalenedione m.p. 107°–108° C.

N.M.R. (CDCl$_3$) δ: 1.45 (3H, s), 2.36 (3H, s), 2.1–3.2 (8H, m), 5.83 (1H, s), 7.2 (4H, bs), 7.53 (1H, bs).

Found M$^+$, 280.1469. Calc. for C$_{19}$H$_{20}$O$_2$, 280.1464.

EXAMPLE 13

4-[(3,4,8,8a-Tetrahydro-8a-methyl-1,6-dioxo(2H,7H)-naphthalen-2-yl)methylidene]benzoic acid m.p. 200°–203° C.

N.M.R. (CDCl$_3$/(CD$_3$)SO) δ: 1.46 (3H, s), 2.0–3.2 (8H, m), 5.83 (1H, s), 7.5 (1H, m), 7.66 (4H, q).

EXAMPLE 14

6-Benzylidene-4,4a,5,6,7,8-hexahydro-5-hydroxy-4a-methyl-2(3H)-naphthalenone m.p. 123°–5° C.

N.M.R. (CDCl$_3$) δ: 1.18 (3H, s), 1.7–2.7 (8H, m), 4.0 (1H, s), 5.73 (1H, s), 6.64 (1H, s), 7.2 (5H, s).

Found M$^+$, 268.1472. Calc. for C$_{18}$H$_{20}$O$_2$, 268.1463.

EXAMPLE 15

6-Benzylidene-4,4a,5,6,7,8-hexahydro-5-hydroxy-4a,5-dimethyl-2(3H)-naphthalenone m.p. 132°–4° C.

N.M.R. (CDCl$_3$) δ: 1.26 (3H, s), 1.42 (3H, s), 1.8–3.2 (8H, m), 5.85 (1H, bs), 6.8 (1H, bs), 7.26 (5H, m).

Found M$^+$, 282.1599. Calc. for C$_{19}$H$_{22}$O$_2$, 282.1620.

EXAMPLE 16

2-(3,4-Dihydroxybenzylidene)-3,4,8,8a-tetrahydro-8a-methyl-1,6(2H,7H)-naphthalenedione

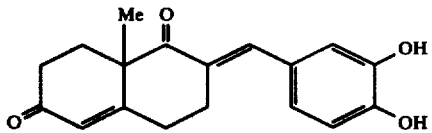

(16)

A solution of boron tribromide (0.28 ml, 0.003 mole) in dichloromethane (15.1) was added to a well stirred solution of 2-(3,4-methylenedioxybenzylidene)-3,4,8,8a-tetrahydro-8a-methyl-1,6(2H,7H)-naphthalenedione (9) (0.3 g, 0.001 mole) in dichloromethane (20 ml) containing potassium carbonate (1.0 g) at −78° C. under nitrogen. After 10 minutes the mixture was treated with methanol (1 ml) and poured into water. The organic phase was separated and dried (Na$_2$SO$_4$). The solvent was removed and the product was chromatographed on silica gel using ether as eluant. The title compound was obtained as a yellow crystalline solid (0.05 g, 17%) m.p. 193°–5° C.

N.M.R. (CD$_3$OD) δ: 1.5 (3H, s), 2.0–2.9 (8H, m), 5.92 (1H, s), 6.75–7.05 (3H, m), 7.51 (1H, bs).

Found M$^+$, 298.1189. Calc. for C$_{18}$H$_{18}$O$_4$, 298.1205.

EXAMPLE 17

2-Benzyl-3,4,8,8a-tetrahydro-8a-methyl-1,6(2H,7H)-naphthalenedione

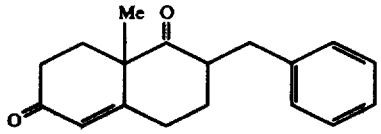

(17)

A solution of 3,4,8,8a-tetrahydro-8a-methyl-1,6(2H,7H)-naphthalenedione (2.5 g, 0.014 mole) in dry tetrahydrofuran (20 ml) was added to lithium diisopropylamide [made from dry diisopropylamine (1.95 ml 0.014 mole) and n-butyl-lithium (12.0 ml of a 1.15 M solution in hexane, 0.014 mole)] at −65° C. under nitrogen. The solution was allowed to warm to 0° C. and a solution of benzyl bromide (2.39 g, 0.014 mole) in dry tetrahydrofuran (6 ml) was added. This was stirred at room temperature overnight, poured into water and extracted with diethyl ether (100 ml). The organic phase was washed with 1 N hydrochloric acid (50 ml) and water (50 ml), then dried ($Na_2SO_4$) and evaporated to give a dark oil. This was chromatographed on silica gel using diethyl ether/petroleum ether (1:1) as eluant giving the title compound which was further purified by distillation b.p. 190° C./0.01 mm. The product was isolated as a mixture of isomers.

N.M.R. ($CDCl_3$) δ: 1.35, 1.46 (3H, s, s), 1.5–3.65 (11H, m), 3.58, 5.85 (1H, bs, bs), 7.25 (5H, m).

Found M+, 268.1475. Calc. for $C_{18}H_{20}O_2$, 268.1464.

PHARMACOLOGICAL DATA

Compounds were tested for anti-inflammatory activity in a topical model based on that described by Fregnan G. B. and Torsello, A. L. (1975), Current Therapeutic Research 17, No. 4, 375–381. In outline the method is as follows:

Rats, Charles River Wistar Strain, female, 10/group. Weight range 200–240 g.

Irritant solution applied consists of 1% croton oil in tetrahydrofuran. 0.05 ml is placed on each ear, compound being included in the irritant solution on one ear. 6 hours later the ears are removed by cutting along the hairline and weighed.

−ve controls—no irritant solution.

+ve controls—irritant solution on both ears.

The results are as shown in Table 2.

Significantly different from the control assessed by the Students 't' test.

**** $p < 0.001$
*** $p < 0.01$
** $p < 0.02$
* $p < 0.05$

TABLE 2

| Compound; Dose, mg/Ear | | Treated Ear | | Non-Treated Ear | |
|---|---|---|---|---|---|
| | | wt. mg | % inhibition | wt. mg | % inhibition |
| −ve control | | 95.2 ± 4.10 | | 96.2 ± 3.40 | |
| +ve control | | 133.1 ± 3.58 | | 135.9 ± 4.43 | |
| Compound 1 | 3.0 | **** 106.6 ± 4.32 | 70 | 136.5 ± 5.80 | −1 |
| −ve control | | 78.3 ± 2.99 | | | |
| +ve control | | 123.7 ± 4.87 | | | |
| Compound 2 | 2 | **** 91.5 ± 3.15 | 71 | | |
| −ve control | | 72.1 ± 2.3 | | | |
| +ve control | | 111.8 ± 5.8 | | | |
| Compound 3 | 2 | **** 86.7 ± 2.4 | 63 | | |
| −ve control | | 78.3 | | | |
| +ve control | | 112.3 | | | |
| Compound 4 | 2 | **** 97.5 | 44 | | |
| −ve control | | 78.3 | | | |
| +ve control | | 112.3 | | | |
| Compound 5 | 2 | **** 98.2 | 41 | | |
| −ve control | | 75.2 | | | |
| +ve control | | 100.7 | | | |
| Compound 6 | 2 | *87.2 | 53 | | |
| −ve control | | *** 66.6 | | | |
| +ve control | | 98.0 | | | |
| Compound 7 | 2 | *** 72.6 | 81 | | |
| −ve control | | ** 69.6 | | | |
| −ve control | | 83.1 | | | |
| Compound 8 | 1.5 | ** 69.8 | 99 | | |
| Compound 14 | 1.5 | *** 68.6 | 107 | | |

TABLE 2-continued

| Compound; Dose, mg/Ear | Treated Ear | | Non-Treated Ear | |
| --- | --- | --- | --- | --- |
| | wt. mg | % inhibition | wt. mg | % inhibition |
| −ve control | ****70.6 | | | |
| −ve control | 89.5 | | | |
| Compound 9  2 | ****69.5 | 100 | | |
| Compound 10  2 | ****70.0 | 98 | | |
| Compound 11  2 | ****70.5 | 95 | | |

TOXICITY

No toxic effects were observed in these tests.

We claim:

1. A compound of formula (I):

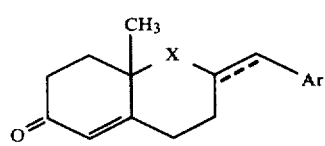

wherein:
Ar is phenyl, optionally substituted by one or more $C_{1-4}$ alkyl, $C_{1-4}$ alkoxy, halogen, nitro, hydroxy or $NR_1R_2$ wherein $R_1$ and $R_2$ are selected from hydrogen or $C_{1-6}$ alkyl;
the dotted lines represent an optionally present double bond; and
X is CO or $CR_1OH$ wherein $R_1$ is hydrogen or $C_{1-4}$ alkyl; or a pharmaceutically acceptable salt thereof.

2. A compound according to claim 1 wherein Ar is phenyl, optionally substituted by $C_{1-4}$ alkyl, $C_{1-4}$ alkoxy or halogen;
the dotted line in formula (I) represents an optionally present double bond; and
X is CO or $CR_1OH$ wherein $R_1$ is hydrogen or $C_{1-4}$ alkyl.

3. A compound according to claim 1 of the formula (IV)

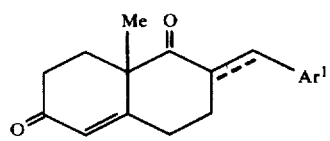

wherein $Ar^1$ is phenyl optionally substituted by one or more $C_{1-4}$ alkyl, $C_{1-4}$ alkoxy, halogen, nitro, hydroxy, or $NR_1R_2$ wherein $R_1$ and $R_2$ are selected from hydrogen or $C_{1-6}$ alkyl.

4. A compound according to claim 3 of the formula (V):

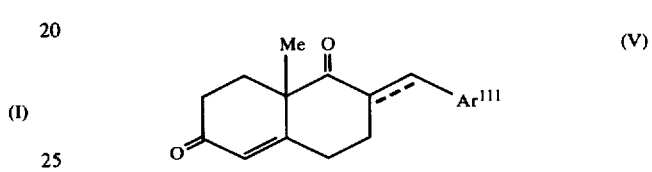

wherein $Ar^{III}$ is phenyl or phenyl substituted by methyl, ethyl, methoxy, chlorine, bromine, or nitro.

5. A compound according to claim 3 of the formula (VI):

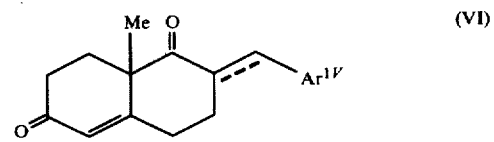

wherein $Ar^{IV}$ is phenyl substituted by hydroxy, or $NR^1_1 R_2^1$ wherein $R^1_1$ and $R^1_2$ are selected from hydrogen and methyl.

6. A compound according to claim 1, characterised in that the exocyclic double bond is present.

7. 2-(4-Dimethylaminobenzylidene)-3,4,8,8a-tetrahydro-8a-methyl-1,6(2H,7H)-naphthalenedione, or 2-(3-hydroxybenzylidene)-3,4,8,8a-tetrahydro-8a-methyl-1,6(2H,7H)-napthalenedione.

8. An anti-inflammatory pharmaceutical composition adapted for topical administration which comprises an effective amount of a compound according to claim 1 or a pharmaceutically acceptable salt thereof and a pharmaceutically acceptable carrier therefor.

9. A method of treatment or prophylaxis of inflammation in mammals including man which comprises the topical administration of a therapeutically effective amount of a compound according to claim 1 or a pharmaceutically acceptable salt thereof.

* * * * *